(12) United States Patent
Vidal et al.

(10) Patent No.: US 6,338,741 B1
(45) Date of Patent: Jan. 15, 2002

(54) COMPOSITION FOR DYEING KERATIN FIBERS WHICH CONTAIN AT LEAST ONE DIAMINOPYRAZOLE, DYEING PROCESS, NOVEL DIAMINOPYRAZOLES AND PROCESS FOR THEIR PREPARATION

(75) Inventors: Laurent Vidal, Paris; Agnès Burande, Villeparisis; Gérard Malle, Meaux; Michel Hocquaux, Paris, all of (FR)

(73) Assignee: L'Oreal (FR)

( * ) Notice: Subject to any disclaimer, the term of this patent is extended or adjusted under 35 U.S.C. 154(b) by 0 days.

(21) Appl. No.: 09/494,762

(22) Filed: Jan. 31, 2000

Related U.S. Application Data

(63) Continuation of application No. 08/642,622, filed on May 3, 1996, now Pat. No. 6,099,592.

(30) Foreign Application Priority Data

May 5, 1995 (FR) .............................................. 95 05422

(51) Int. Cl.$^7$ ........................ A61K 7/13; C07D 231/10
(52) U.S. Cl. ........................... 8/409; 8/423; 548/364.1; 548/365.7; 548/373.1; 548/375.1; 548/376.1; 548/377.1
(58) Field of Search ............................ 8/406, 407, 408, 8/409, 410, 411, 412, 423, 573; 548/371.4, 371.7, 372.5, 364.1, 365.7, 373.1, 375.1, 376.1, 377.1

(56) References Cited

U.S. PATENT DOCUMENTS

| | | | |
|---|---|---|---|
| 5,008,263 A | 4/1991 | Cooper et al. | 514/220 |
| 5,061,289 A | 10/1991 | Claussen et al. | 8/405 |
| 5,389,660 A | 2/1995 | Greenlee et al. | 514/381 |
| 5,430,159 A | 7/1995 | Neunhoeffer et al. | 548/371.4 |
| 5,500,439 A | 3/1996 | Ulrich et al. | 514/404 |

FOREIGN PATENT DOCUMENTS

| | | |
|---|---|---|
| EP | 216 334 | 3/1987 |
| EP | 375 977 | 4/1990 |
| JP | 06-130603 | 5/1994 |
| WO | WO 94/08969 | 4/1994 |
| WO | WO 94/08970 | 4/1994 |
| WO | WO 94/08971 | 4/1994 |

*Primary Examiner*—Margaret Einsmann
(74) *Attorney, Agent, or Firm*—Finnegan, Henderson, Farabow, Garrett & Dunner, L.L.P.

(57) ABSTRACT

The invention relates to novel compositions for the oxidation dyeing of keratin fibers, comprising at least one specific diaminopyrazole derivative, to the dyeing process using this composition, to novel diaminopyrazole derivatives and to a process for their preparation.

3 Claims, No Drawings

COMPOSITION FOR DYEING KERATIN FIBERS WHICH CONTAIN AT LEAST ONE DIAMINOPYRAZOLE, DYEING PROCESS, NOVEL DIAMINOPYRAZOLES AND PROCESS FOR THEIR PREPARATION

This is a continuation of application Ser. No. 08/642,622, filed May 3, 1996, now U.S. Pat. No. 6,099,592.

The invention relates to novel compositions for the oxidation dyeing of keratin fibers, which compositions comprise at least one 3-substituted 4,5-diaminopyrazole as oxidation base, to the dyeing process using this composition, to novel 3-substituted 4,5-diaminopyrazoles and to a process for their preparation.

It is known to dye keratin fibers, and in particular human hair, with dye compositions containing oxidation dye precursors, in particular ortho-or para-phenylenediamines, ortho- or para-aminophenols and heterocyclic compounds such as diaminopyrazole derivatives, which are generally referred to as oxidation bases. The oxidation dye precursors, or oxidation bases, are colorless or weakly colored compounds which, when combined with oxidizing products, may give rise to colored compounds and dyes by a process of oxidative condensation.

It is also known that the shades obtained with these oxidation bases may be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colors.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, inclement weather, washing, permanent-waving, perspiration and friction).

The dyes must also allow white hairs to be covered and, lastly, they must be as unselective as possible, i.e., they must allow the smallest possible differences in coloration to be produced over the entire length of the same keratin fiber, which may indeed be differently sensitized (i.e. damaged) between its tip and its root.

In order to obtain red shades, para-aminophenol is usually used, alone or as a mixture with other bases, and in combination with suitable couplers, and in order to obtain blue shades, para-phenylenediamines are generally used.

European Patent Application EP-A-375,977 in particular has already proposed to use certain diaminopyrazole derivatives, namely, more precisely, 3,4- or 4,5-diaminopyrazoles, for the oxidation dyeing of keratin fibers in red shades. However, the use of the diaminopyrazoles described in EP-A-375,977 do not make it possible to obtain a wide range of colors and, furthermore, the process for the preparation of these compounds is long and expensive.

Now, the inventors have discovered, entirely unexpectedly and surprisingly, that the use of certain 3-substituted 4,5-diaminopyrazoles of formula (I) defined below for the part which is novel per se, is not only suitable for use as oxidation dye precursors but also make it possible to obtain dye compositions leading to strong coloration, in shades ranging from red to blue. Lastly, these compounds prove to be readily synthesizable.

These discoveries form the basis of the present invention.

A first subject of the invention is thus a composition for the oxidation dyeing of keratin fibers, and in particular human keratin fibers such as the hair, characterized in that it comprises, in a medium which is suitable for dyeing, at least one 3-substituted 4,5-diaminopyrazole of formula (I) below as oxidation base and/or at least one of the addition salts thereof with an acid:

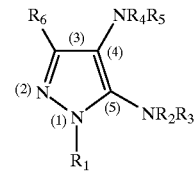

(I)

in which:

$R_1$, $R_2$, $R_3$, $R_4$ and $R_5$ which may be identical or different, represent a hydrogen atom; a linear or branched $C_1$–$C_6$ alkyl radical; a $C_2$–$C_4$ hydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; or a radical:

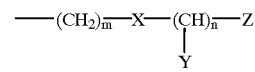

in which m and n are integers, which may be identical or different, from 1 to 3 inclusive, X represents an oxygen atom or the NH group, Y represents a hydrogen atom or a methyl radical and Z represents a methyl radical, a group OR or NRR' in which R and R', which may be identical or different, denote a hydrogen atom, a methyl radical or an ethyl radical, it being understood that when $R_2$ represents a hydrogen atom, $R_3$ may then also represent an amino or $C_1$–$C_4$ alkylamino radical, $R_6$ represents a linear or branched $C_1$–$C_6$ alkyl radical; a $C_1$–$C_4$ hydroxyalkyl radical; a $C_1$–$C_4$ aminoalkyl radical; a $C_1$–$C_4$ dialkylamino ($C_1$–$C_4$) alkyl radical; a $C_1$–$C_4$ alkylamino ($C_1$–$C_4$) alkyl radical; a $C_1$–$C_4$ hydroxyalkylamino ($C_1$–$C_4$) alkyl radical; a $C_1$–$C_4$ alkoxymethyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, nitro, trifluoromethyl, amino or $C_1$–$C_4$ alkylamino radical; a heterocycle chosen from thiophene, furan and pyridine, or alternatively a radical —$(CH_2)_p$—O—$(CH_2)_q$—OR", in which p and q are integers, which may be identical or different, from 1 to 3 inclusive and R" represents a hydrogen atom or a methyl radical, it being understood that, in the above formula (I):

at least one of the radicals $R_2$, $R_3$, $R_4$ and $R_5$ represents a hydrogen atom, when $R_2$, or respectively $R_4$, represents a substituted or unsubstituted phenyl radical or a benzyl radical or a radical

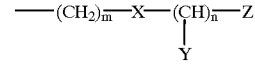

$R_3$, or respectively $R_5$, cannot then represent any of these three radicals, when $R_4$ and $R_5$ simultaneously represent a hydrogen atom, $R_1$ can then form, with $R_2$ and $R_3$, a hexahydropyrimidine or tetrahydroimidazole heterocycle optionally substituted with a $C_1$–$C_4$ alkyl or 1,2,4-tetrazole radical, when $R_2$, $R_3$, $R_4$ and $R_5$ represent a hydrogen atom or a $C_1$–$C_6$ alkyl radical, $R_1$ or $R_6$ may then also represent a 2-, 3- or 4-pyridyl, 2- or 3-thienyl or 2- or 3-furyl heterocyclic residue optionally substituted with a methyl radical or alternatively a cyclohexyl radical.

As indicated above, the colorations obtained with the oxidation dye composition in accordance with the invention are strong and make it possible to achieve shades ranging from red to blue. One of the essential characteristics of the oxidation bases in accordance with the invention in particular relative to those described in the abovementioned document EP-A 375,977, lies in the presence of a substituent radical $R_6$ on the pyrazole ring.

In general, the addition salts with an acid which can be used in the context of the dye compositions of the invention (oxidation bases and couplers) are chosen in particular from the hydrochlorides, hydrobromides, sulphates, tartrates, lactates and acetates.

Among the 3-substituted 4,5-diaminopyrazoles of formula (I) which can be used as oxidation base in the compositions in accordance with the invention, mention may be made, in particular, of:

1-benzyl-4,5-diamino-3-methylpyrazole,
4,5-diamino-1-(β-hydroxyethyl)-3-(4'-methoxyphenyl)-pyrazole,
4,5-diamino-1-(β-hydroxyethyl)-3-(4'-methylphenyl)-pyrazole,
4,5-diamino-1-(β-hydroxyethyl)-3-(4'-methylphenyl)-pyrazole,
4,5-diamino-3-methyl-1-isopropylpyrazole,
4,5-diamino-3-(4'-methoxyphenyl)-1-isopropyl-pyrazole,
4,5-diamino-1-ethyl-3-methylpyrazole,
4,5-diamino-1-ethyl-3-(4'-methoxyphenyl)pyrazole,
4,5-diamino-3-hydroxymethyl-1-methylpyrazole,
4,5-diamino-1-ethyl-3-hydroxymethylpyrazole,
4,5-diamino-3-hydroxymethyl-1-isopropylpyrazole,
4,5-diamino-3-hydroxymethyl-1-tert-butylpyrazole,
4,5-diamino-3-hydroxymethyl-1-phenylpyrazole,
4,5-diamino-3-hydroxymethyl-1-(2'-methoxyphenyl)-pyrazole,
4,5-diamino-3-hydroxymethyl-1-(3'-methoxyphenyl)-pyrazole,
4,5-diamino-3-hydroxymethyl-1-(4'-methoxyphenyl)-pyrazole,
1-benzyl-4,5-diamino-3-hydroxymethylpyrazole,
4,5-diamino-3-methyl-1-(2'-methoxyphenyl)pyrazole,
4,5-diamino-3-methyl-1-(3'-methoxyphenyl)pyrazole,
4,5-diamino-3-methyl-1-(4'-methoxyphenyl)pyrazole,
3-aminomethyl-4,5-diamino-1-methylpyrazole,
3-aminomethyl-4,5-diamino-1-ethylpyrazole,
3-aminomethyl-4,5-diamino-1-isopropylpyrazole,
3-aminomethyl-4,5-diamino-1-tert-butylpyrazole,
4,5-diamino-3-dimethylaminomethyl-1-methylpyrazole,
4,5-diamino-3-dimethylaminomethyl-1-ethylpyrazole,
4,5-diamino-3-dimethylaminomethyl-1-isopropyl-pyrazole,
4,5-diamino-3-dimethylaminomethyl-1-tert-butyl-pyrazole,
4,5-diamino-3-ethylaminomethyl-1-methylpyrazole,
4,5-diamino-3-ethylaminomethyl-1-ethylpyrazole,
4,5-diamino-3-ethylaminomethyl-1-isopropylpyrazole,
4,5-diamino-3-ethylaminomethyl-1-tert-butylpyrazole,
4,5-diamino-3-methylaminomethyl-1-methylpyrazole,
4,5-diamino-3-methylaminomethyl-1-isopropylpyrazole,
4,5-diamino-1-ethyl-3-methylaminomethylpyrazole,
1-tert-butyl-4,5-diamino-3-methylaminomethyl-pyrazole,
4,5-diamino-3-[(β-hydroxyethyl)aminomethyl]-1-methylpyrazole,
4,5-diamino-3-[(β-hydroxyethyl)aminomethyl]-1-isopropylpyrazole,
4,5-diamino-1-ethyl-3-[(β-hydroxyethyl)aminomethyl]-pyrazole,
1-tert-butyl-4,5-diamino-3-[(β-hydroxyethyl)aminomethyl]pyrazole,
4-amino-5-(β-hydroxyethyl)amino-1,3-dimethylpyrazole,
4-amino-5-(β-hydroxyethyl)amino-1-isopropyl-3-methyl-pyrazole,
4-amino-5-(β-hydroxyethyl)amino-1-ethyl-3-methyl-pyrazole,
4-amino-5-(β-hydroxyethyl)amino-1-tert-butyl-3-methylpyrazole,
4-amino-5-(β-hydroxyethyl)amino-1-phenyl-3-methyl-pyrazole,
4-amino-5-(β-hydroxyethyl)amino-1-(2'-methoxyphenyl)-3-methylpyrazole,
4-amino-5-(β-hydroxyethyl)amino-1-(3'-methoxyphenyl)-3-methylpyrazole,
4-amino-5-(β-hydroxyethyl)amino-1-(4'-methoxyphenyl)-3-methylpyrazole,
4-amino-5-(β-hydroxyethyl)amino-1-benzyl-3-methyl-pyrazole,
4-amino-1-ethyl-3-methyl-5-methylaminopyrazole,
4-amino-1-tert-butyl-3-methyl-5-methylaminopyrazole,
4,5-diamino-1,3-dimethylpyrazole,
4,5-diamino-3-tert-butyl-1-methylpyrazole,
4,5-diamino-1-tert-butyl-3-methylpyrazole,
4,5-diamino-1-methyl-3-phenylpyrazole,
4,5-diamino-1-(β-hydroxyethyl)-3-methylpyrazole,
4,5-diamino-1-(β-hydroxyethyl)-3-phenylpyrazole,
4,5-diamino-1-methyl-3-(2'-chlorophenyl)pyrazole,
4,5-diamino-1-methyl-3-(4'-chlorophenyl)pyrazole,
4,5-diamino-1-methyl-3-(3'-trifluoromethylphenyl)-pyrazole,
4,5-diamino-1,3-diphenylpyrazole,
4,5-diamino-3-methyl-1-phenylpyrazole,
4-amino-1,3-dimethyl-5-phenylaminopyrazole,
4-amino-1-ethyl-3-methyl-5-phenylaminopyrazole,
4-amino-1,3-dimethyl-5-methylaminopyrazole,
4-amino-3-methyl-1-isopropyl-5-methylaminopyrazole,
4-amino-3-isobutoxymethyl-1-methyl-5-methylamino-pyrazole,
4-amino-3-methoxyethoxymethyl-1-methyl-5-methylamino-pyrazole,
4-amino-3-hydroxymethyl-1-methyl-5-methylamino-pyrazole,
4-amino-1,3-diphenyl-5-phenylaminopyrazole,
4-amino-3-methyl-5-methylamino-1-phenylpyrazole,
4-amino-1,3-dimethyl-5-hydrazinopyrazole,
5-amino-3-methyl-4-methylamino-1-phenylpyrazole,
5-amino-1-methyl-4-(N-methyl-N-phenyl)amino-3-(4'-chlorophenyl)pyrazole,
5-amino-3-ethyl-1-methyl-4-(N-methyl-N-phenyl)amino-pyrazole,
5-amino-1-methyl-4-(N-methyl-N-phenyl)amino-3-phenyl-pyrazole,
5-amino-3-ethyl-4-(N-methyl-N-phenyl)aminopyrazole,
5-amino-4-(N-methyl-N-phenyl)amino-3-phenylpyrazole,
5-amino-4-(N-methyl-N-phenyl)amino-3-(4'-methylphenyl)pyrazole,
5-amino-3-(4'-chlorophenyl)-4-(N-methyl-N-phenyl)aminopyrazole,
5-amino-3-(4'-methoxyphenyl)-4-(N-methyl-N-phenyl)aminopyrazole,
4-amino-5-methylamino-3-phenylpyrazole,
4-amino-5-ethylamino-3-phenylpyrazole,
4-amino-5-ethylamino-3-(4'-methylphenyl)pyrazole,
4-amino-3-phenyl-5-propylaminopyrazole,
4-amino-5-butylamino-3-phenylpyrazole,
4-amino-3-phenyl-5-phenylaminopyrazole, 1-tert-butyl-4,5-diamino-3-[(β-hydroxyethyl)amino-methyl]pyrazole, 4-amino-5-butylamino-3-phenylpyrazole,
4-amino-5-(4'-chlorophenyl)amino-3-phenylpyrazole,
4-amino-3-(4'-chlorophenyl)-5-phenylaminopyrazole,
4-amino-3-(4'-methoxyphenyl)-5-phenylaminopyrazole,
1-(4'-chlorobenzyl)-4,5-diamino-3-methylpyrazole,
4,5-diamino-3-hydroxymethyl-1-isopropylpyrazole,
4-amino-1-ethyl-3-methyl-5-methylaminopyrazole,
4-amino-5-(2'-aminoethyl)amino-1,3-dimethyl-pyrazole,
and the addition salts thereof with an acid.

Among these 3-substituted 4,5-diaminopyrazoles, the following are more particularly preferred:
4,5-diamino-1,3-dimethylpyrazole,
4,5-diamino-3-methyl-1-phenylpyrazole,
4,5-diamino-1-methyl-3-phenylpyrazole,
4-amino-1,3-dimethyl-5-hydrazinopyrazole,
1-benzyl-4,5-diamino-3-methylpyrazole,
4,5-diamino-3-tert-butyl-1-methylpyrazole,
4,5-diamino-1-tert-butyl-3-methylpyrazole,
4,5-diamino-1-($\beta$-hydroxyethyl)-3-methylpyrazole,
4,5-diamino-1-ethyl-3-methylpyrazole,
4,5-diamino-1-ethyl-3-(4'-methoxyphenyl)pyrazole,
4,5-diamino-1-ethyl-3-hydroxymethylpyrazole,
4,5-diamino-3-hydroxymethyl-1-methylpyrazole,
4,5-diamino-3-hydroxymethyl-1-isopropylpyrazole,
4,5-diamino-3-methyl-1-isopropylpyrazole,
4-amino-5-(2'-aminoethyl)amino-1,3-dimethylpyrazole,
and the addition salts thereof with an acid.

The 3-substituted 4,5-diaminopyrazole(s) of formula (I) above preferably represent from 0.0005 to 12% by weight approximately relative to the total weight of the dye composition, and even more preferably from 0.005 to 6% by weight approximately relative to this weight.

The appropriate medium for the dyeing (or the support) generally comprises water or a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monomethyl ether and monoethyl ether, as well as aromatic alcohols such as benzyl alcohol or phenoxyethanol, similar products and mixtures thereof.

The solvents may be present in proportions preferably of approximately from 1 to 40% by weight relative to the total weight of the dye composition, and even more preferably of approximately from 5 to 30% by weight.

The pH of the dye composition in accordance with the invention is generally from 3 to 12 and preferably is approximately from 5 to 11. It may be adjusted to the desired value using acidifying or basifying agents usually used in the dyeing of keratin fibers.

Among the acidifying agents which may be mentioned, by way of example, are inorganic or organic acids such as hydrochloric acid, orthophosphoric acid, sulfuric acid, carboxylic acids such as acetic acid, tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and the compounds of following formula (II):

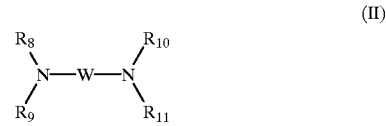

(II)

in which W is a propylene residue optionally substituted with a hydroxyl group or a $C_1$–$C_4$ alkyl radical; $R_8$, $R_9$, $R_{10}$ and $R_{11}$, which may be identical or different, represent a hydrogen atom or a $C_1$–$C_4$ alkyl or $C_1$–$C_4$ hydroxyalkyl radical.

In addition to the dyes defined above, the dye composition in accordance with the invention may also contain at least one additional oxidation base which may be chosen from the oxidation bases conventionally used in oxidation dyeing and from which mention may be made, in particular, of para-phenylenediamines, bis(phenylalkylenediamines), para-aminophenols, ortho-aminophenols and heterocyclic bases other than the 3-substituted 4,5-diaminopyrazoles used in accordance with the invention.

Among the para-phenylenediamines which may be mentioned more particularly as examples are para-phenylenediamine, para-toluylenediamine, 2,6-dimethyl-para-phenylenediamine, 2-$\beta$-hydroxyethyl-para-phenylenediamine, 2-n-propyl-para-phenylenediamine, 2-isopropyl-para-phenylenediamine, N-($\beta$-hydroxypropyl)-para-phenylenediamine, N,N-bis($\beta$-hydroxyethyl)-para-phenylenediamine, 4-amino-N-($\beta$-methoxyethyl)aniline, the para-phenylenediamines described in French patent application FR 2,630,438, the disclosure of which is hereby incorporated by reference, and the addition salts thereof with an acid.

Among the bis(phenylalkylenediamines) which may be mentioned more particularly as examples are N,N'-bis($\beta$-hydroxyethyl)-N,N'-bis(4'-aminophenyl)-1,3-diaminopropanol, N,N'-bis($\beta$-hydroxyethyl)-N,N'-bis(4'-aminophenyl)ethylenediamine, N,N'-bis(4-aminophenyl)-tetramethylenediamine, N,N'-bis($\beta$-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and the addition salts thereof with an acid.

Among the para-aminophenols which may be mentioned more particularly as examples are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-($\beta$-hydroxyethylaminomethyl)phenol, and the addition salts thereof with an acid.

Among the ortho-aminophenols which may be mentioned more particularly as examples are 2-aminophenol, 2-amino-5-methylphenol, 2-amino-6-methylphenol, 5-acetamido-2-aminophenol, and the addition salts thereof with an acid.

Among the heterocyclic bases which may be mentioned more particularly as examples are pyridine derivatives, pyrimidine derivatives, pyrazole derivatives other than the 3-substituted 4,5-diaminopyrazoles used in accordance with the invention, and the addition salts thereof with an acid.

When they are used, these additional oxidation bases preferably represent from 0.0005 to 12% by weight approximately relative to the total weight of the dye composition, and even more preferably from 0.005 to 6% by weight approximately relative to this weight.

The oxidation dye compositions in accordance with the invention may also contain at least one coupler and/or at least one direct dye, in particular to modify the shades or enrich them with glints.

The couplers which can be used in the oxidation dye compositions in accordance with the invention may be chosen from the couplers used conventionally in oxidation dyeing and among which mention may be made in particular of meta-phenylenediamines, meta-aminophenols, meta-diphenols and heterocyclic couplers such as, for example, indole derivatives, indoline derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methyl-5-pyrazolone, 1-phenyl-3-methyl-5-pyrazolone, and the addition salts thereof with an acid.

When they are present, these couplers preferably represent from 0.0001 to 10% by weight approximately relative to the total weight of the dye composition, and even more preferably from 0.005 to 5% by weight approximately relative to this weight.

The dye composition according to the invention may also contain various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Obviously, a person skilled in the art will take care to select this or these optional complementary compounds such that the advantageous properties intrinsically attached to the oxidation dye composition in accordance with the invention are not, or are substantially not, damaged by the additions envisaged.

The dye composition according to the invention may be in various forms, such as in the form of liquids, creams or gels or any other form which is suitable for dyeing keratin fibers, and in particular human hair.

The subject of the invention is also a process for dyeing keratin fibers, and in particular human keratin fibers such as the hair, which uses the dye composition as defined above.

According to this process, at least one dye composition as defined above is applied to the fibers, for a period which is sufficient to develop the desired coloration, either in air or with the aid of an oxidizing agent.

According to a first embodiment of the process of the invention, the fibers may be dyed without addition of an oxidizing agent, merely by contact with atmospheric oxygen. In this case, the dye composition may then optionally contain oxidation catalysts, so as to accelerate the oxidation process.

Oxidation catalysts which may be mentioned more particularly are metal salts such as manganese, cobalt, copper, iron, silver and zinc salts.

Such compounds are, for example, manganese diacetate tetrahydrate, manganese dichloride and its hydrates, manganese dihydrogen carbonate, manganese acetylacetonate, manganese triacetate and its hydrates, manganese trichloride, zinc dichloride, zinc diacetate dihydrate, zinc carbonate, zinc dinitrate, zinc sulphate, iron dichloride, iron sulphate, iron diacetate, cobalt diacetate tetrahydrate, cobalt carbonate, cobalt dichloride, cobalt dinitrate, cobalt sulphate heptahydrate, cupric chloride and ammoniacal silver nitrate.

The manganese salts are particularly preferred.

When they are used, these metal salts are generally used in proportions ranging from 0.001 to 4% by weight of metal equivalent relative to the total weight of the dye composition, and preferably from 0.005 to 2% by weight of metal equivalent relative to the total weight of the dye composition.

According to a second embodiment of the process of the invention, at least one dye composition as defined above is applied to the fibers, the colour being developed at acidic, neutral or alkaline pH using an oxidizing agent which is added, only at the time of use, to the dye composition or which is present in an oxidizing composition that is applied simultaneously or sequentially in a separate manner.

According to this second embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibers and is generally left in place for 3 to 50 minutes approximately, preferably for 5 to 30 minutes approximately, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibers preferably ranges from 3 to 12 approximately, and even more preferably from 5 to 11. It is adjusted to the desired value using acidifying or basifying agents usually used in the dyeing of keratin fibers and as defined above.

The oxidizing composition as defined above may also contain various adjuvants conventionally used in compositions for dyeing the hair and as defined above.

The composition which is finally applied to the keratin fibers may be in various forms, such as in the form of liquids, creams or gels or in any other form which is suitable for dyeing keratin fibers, and in particular human hair.

Another subject of the invention is a multi-compartment device or dyeing kit or any other multi-compartment packaging system, a first compartment of which contains the dye composition as defined above and a second compartment of which contains the oxidizing composition as defined above. These devices may be equipped with a means which makes it possible to deliver the desired mixture onto the hair, such as the devices described in French patent FR-2,586,913 in the name of the present assignee, the disclosure of which is hereby incorporated by reference.

Certain compounds of formula (I), used as oxidation base in the context of the present invention, are novel and, in this respect, constitute another subject of the invention.

These novel 3-substituted 4,5-diamino-pyrazoles and the addition salts thereof with an acid correspond to the following formula (I'):

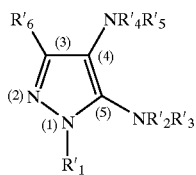

(I')

in which R'$_1$, R'$_2$, R'$_3$, R'$_4$, R'$_5$ and R'$_6$ have the same meanings as those indicated above for the radicals R$_1$, R$_2$, R$_3$, R$_4$, R$_5$ and R$_6$ in the formula (I), with, however, the following provisos:

(i) when R'$_1$ represents a methyl radical, and when R'$_2$, R'$_4$ and R'$_5$ simultaneously represent a hydrogen atom, and when R'$_3$ represents a hydrogen atom or a methyl radical, R'$_6$ is then other than a hydroxymethyl, isobutyloxymethyl, methoxyethyloxymethyl, cyclohexyl, thiophene, pyridine or phenyl radical or phenyl radical substituted with a methyl radical or with a trifluoromethyl radical or with a chlorine atom;

(ii) when R'$_1$ represents an unsubstituted phenyl radical and when R'$_2$, R'$_3$, R'$_4$ and R'$_5$ simultaneously represent a hydrogen atom, R'$_6$ is then other than an unsubstituted phenyl radical;

(iii) when R'$_1$ represents an unsubstituted phenyl radical, and when R'$_6$ represents a methyl radical, and when R'$_2$, R'$_4$ and R'$_5$ simultaneously represent a hydrogen atom, R'$_3$ is then other than a hydrogen atom, a methyl radical or an unsubstituted phenyl radical;

(iv) when R'$_1$ represents an unsubstituted phenyl radical, and when R'$_6$ represents a methyl radical, and when R'$_4$ and R'$_5$ simultaneously represent a hydrogen atom, and when R'$_2$ represents a methyl or ethyl radical, R'$_3$ is then other than an unsubstituted phenyl radical;

(v) when R'$_1$ represents an unsubstituted phenyl radical, and when R'$_6$ represents a methyl radical, and R'$_2$, R'$_3$ and R'$_5$ simultaneously represent a hydrogen atom, R'$_4$ is then other than a methyl radical;

(vi) when R'$_2$, R'$_3$, R'$_4$ and R'$_5$ simultaneously represent a hydrogen atom, and when R'$_6$ represents a methyl radical, R'$_1$ is then other than a phenyl radical substituted with a chlorine atom or with a trifluoroethyl, nitro or pyridyl radical;

(vii) when R'$_1$ represents a hydrogen atom, and when R'$_6$ represents a phenyl radical or a phenyl radical substituted with a chlorine atom or with a methyl or methoxy radical, and when R'$_2$, R'$_4$ and R'$_5$ simultaneously represent a hydrogen atom, R'$_3$ is then other than a hydrogen atom or a C$_1$–C$_4$ alkyl or unsubstituted phenyl radical;

(viii) when R'$_1$, R'$_2$, R'$_3$, R'$_4$ and R'$_5$ simultaneously represent a hydrogen atom, R'$_6$ is then other than a methyl radical;

(ix) when R'$_1$ represents a β-hydroxyethyl radical, and when R'$_2$, R'$_3$, R'$_4$ and R'$_5$ simultaneously represent a hydrogen atom, R'$_6$ is then other than a methyl or unsubstituted phenyl radical;

(x) when R'$_4$ represents a methyl radical, and when R'$_5$ represents an unsubstituted phenyl radical, and when R'$_2$ and R'$_3$ simultaneously represent a hydrogen atom, and when R'$_1$ represents a hydrogen atom or a methyl radical, R'$_6$ is then other than an unsubstituted phenyl radical or a phenyl radical substituted with a methyl, ethyl or methoxy radical or with a chlorine atom;

(xi) when R'$_1$ represents a tert-butyl radical, and when R'$_2$, R'$_3$, R'$_4$ and R'$_5$ simultaneously represent a hydrogen atom, R'$_6$ is then other than a methyl radical;

(xii) when R'$_1$ represents a pyridyl radical, and when R'$_2$, R'$_4$ and R'$_5$ simultaneously represent a hydrogen atom, and when R'$_3$ represents a hydrogen atom or a methyl radical, R'$_6$ is then other than a methyl or unsubstituted phenyl radical;

(xiii) when R'$_1$ represents a methyl, ethyl or 4-aminophenyl radical, and when R'$_2$, R'$_4$ and R'$_5$ simultaneously represent a hydrogen atom, and when R'$_3$ represents a hydrogen atom or an unsubstituted phenyl radical, R'$_6$ is then other than a methyl radical;

(xiv) when R'$_1$ represents an isopropyl radical, and when R'$_2$, R'$_4$ and R'$_5$ simultaneously represent a hydrogen atom, at least one of the radicals R'$_3$ and R'$_6$ is then other than a methyl radical;

(xv) when R'$_1$ represents a hydrogen atom or an unsubstituted phenyl radical, and when R'$_2$, R'$_4$ and R'$_5$ simultaneously represent a hydrogen atom, and when R'$_3$ represents a benzyl radical or a phenyl radical substituted with a methyl radical or with a chlorine atom, R'$_6$ is then other than a methyl or unsubstituted phenyl radical.

Among the novel compounds of formula (I') which may be mentioned in particular are:
1-benzyl-4,5-diamino-3-methylpyrazole,
4,5-diamino-1-(β-hydroxyethyl)-3-(4'-methoxyphenyl)-pyrazole,
4,5-diamino-1-(β-hydroxyethyl)-3-(4'-methylphenyl)-pyrazole,
4,5-diamino-1-(β-hydroxyethyl)-3-(3'-methylphenyl)-pyrazole,
4,5-diamino-3-methyl-1-isopropylpyrazole,
4,5-diamino-3-(4'-methoxyphenyl)-1-isopropyl-pyrazole,
4,5-diamino-1-ethyl-3-methylpyrazole,
4,5-diamino-1-ethyl-3-(4'-methoxyphenyl)pyrazole,
4,5-diamino-3-hydroxymethyl-1-methylpyrazole,
4,5-diamino-1-ethyl-3-hydroxymethylpyrazole,
4,5-diamino-3-hydroxymethyl-1-isopropylpyrazole,
4,5-diamino-3-hydroxymethyl-1-tert-butylpyrazole,
4,5-diamino-3-hydroxymethyl-1-phenylpyrazole,
4,5-diamino-3-hydroxymethyl-1-(2'-methoxyphenyl)-pyrazole,
4,5-diamino-3-hydroxymethyl-1-(3'-methoxyphenyl)-pyrazole,
4,5-diamino-3-hydroxymethyl-1-(4'-methoxyphenyl)-pyrazole,
1-benzyl-4,5-diamino-3-hydroxymethylpyrazole,
4,5-diamino-3-methyl-1-(2'-methoxyphenyl)pyrazole,
4,5-diamino-3-methyl-1-(3'-methoxyphenyl)pyrazole,
4,5-diamino-3-methyl-1-(4'-methoxyphenyl)pyrazole,
3-aminomethyl-4,5-diamino-1-methylpyrazole,
3-aminomethyl-4,5-diamino-1-ethylpyrazole,
3-aminomethyl-4,5-diamino-1-isopropylpyrazole,
3-aminomethyl-4,5-diamino-1-tert-butylpyrazole,
4,5-diamino-3-dimethylaminomethyl-1-methylpyrazole,
4,5-diamino-3-dimethylaminomethyl-1-ethylpyrazole,
4,5-diamino-3-dimethylaminomethyl-1-isopropyl-pyrazole,
4,5-diamino-3-dimethylaminomethyl-1-tert-butyl-pyrazole,
4,5-diamino-3-ethylaminomethyl-1-methylpyrazole,
4,5-diamino-3-ethylaminomethyl-1-ethylpyrazole,
4,5-diamino-3-ethylaminomethyl-1-isopropylpyrazole,
4,5-diamino-3-ethylaminomethyl-1-tert-butylpyrazole,
4,5-diamino-3-methylaminomethyl-1-methylpyrazole,
4,5-diamino-3-methylaminomethyl-1-isopropylpyrazole,
4,5-diamino-1-ethyl-3-methylaminomethylpyrazole,
1-tert-butyl-4,5-diamino-3-methylaminomethyl-pyrazole,
4,5-diamino-3-[(β-hydroxyethyl)aminomethyl]-1-methyl-pyrazole,
4,5-diamino-3-[(β-hydroxyethyl)aminomethyl]-1-isopropylpyrazole, 4,5-diamino-1-ethyl-3-[(β-hydroxyethyl)aminomethyl]-pyrazole,
1-tert-butyl-4,5-diamino-3-[(β-hydroxyethyl)aminomethyl]pyrazole,
4-amino-5-(β-hydroxyethyl)amino-1,3-dimethylpyrazole,
4-amino-5-(β-hydroxyethyl)amino-1-isopropyl-3-methylpyrazole,
4-amino-5-(β-hydroxyethyl)amino-1-ethyl-3-methylpyrazole,
4-amino-5-(β-hydroxyethyl)amino-1-tert-butyl-3-methylpyrazole,
4-amino-5-(β-hydroxyethyl)amino-1-phenyl-3-methylpyrazole,
4-amino-5-(β-hydroxyethyl)amino-1-(2'-methoxyphenyl)-3-methylpyrazole,
4-amino-5-(β-hydroxyethyl)amino-1-(3'-methoxyphenyl)-3-methylpyrazole,
4-amino-5-(β-hydroxyethyl)amino-1-(4'-methoxyphenyl)-3-methylpyrazole,
4-amino-5-(β-hydroxyethyl)amino-1-benzyl-3-methylpyrazole,
4-amino-1-ethyl-3-methyl-5-methylaminopyrazole,
4-amino-1-tert-butyl-3-methyl-5-methylaminopyrazole,
1-(4'-chlorobenzyl)-4,5-diamino-3-methylpyrazole,
4,5-diamino-3-hydroxymethyl-1-isopropylpyrazole,
4-amino-1-ethyl-3-methyl-5-methylaminopyrazole,
4-amino-5-(2'-aminoethyl)amino-1,3-dimethylpyrazole,
and the addition salts thereof with an acid.

Among the novel compounds of formula (I') which are more particularly preferred are:
1-benzyl-4,5-diamino-3-methylpyrazole,
4,5-diamino-1-ethyl-3-methylpyrazole,
4,5-diamino-1-ethyl-3-(4'-methoxyphenyl)pyrazole,
4,5-diamino-1-ethyl-3-hydroxymethylpyrazole,
4,5-diamino-3-hydroxymethyl-1-methylpyrazole,
4,5-diamino-3-hydroxymethyl-1-isopropylpyrazole,
4,5-diamino-3-methyl-1-isopropylpyrazole,
4-amino-5-(2'-aminoethyl)amino-1,3-dimethyl-pyrazole,
and the addition salts thereof with an acid.

The subject of the invention is also processes for the preparation of the novel compounds of formula (I').

When $R'_6$ represents a methyl radical, and when $R'_1$ is other than a hydrogen atom, (compounds of formula (I'A) below), process A corresponding to the following synthetic scheme:

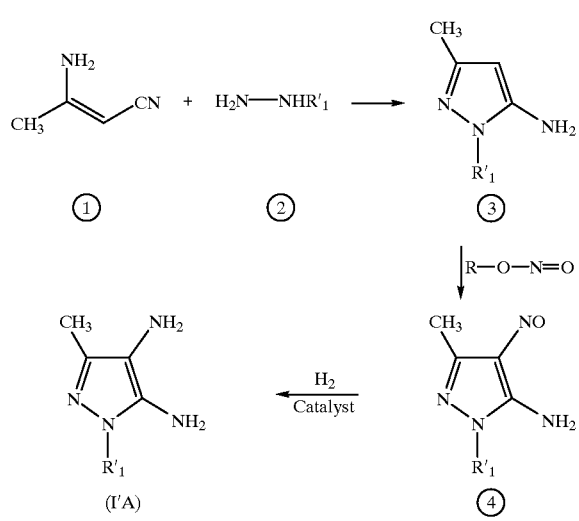

is preferably used, this reaction scheme comprising reacting, in a first step, a 3-aminocrotononitrile (1) with a monosubstituted hydrazine (2), at a temperature generally above 90° C., and preferably from 95 to 150° C., in an alcoholic solvent, followed, in a second step, in nitrosing the 5-aminopyrazole (3) in the 4-piston, by reaction with an inorganic or organic nitrite, in order to give the 5-amino 4-nitrosopyrazole (4) which leads, in a third step, by catalytic hydrogenation to the 4,5-diaminopyrazoles of formula (I'A).

In order to have good control over the temperature during the first step, it is generally preferred to work at the reflux temperature of the solvent used. Among the alcohols used as reaction solvent which may be mentioned more particularly are n-propanol, 1-butanol, 1-butanol, 2-methyl-2-butanol, 3-methyl-1-butanol, 2-methyl-1-propanol, n-pentanol, 2-pentanol, 3-methyl-3-pentanol, 4-methyl-2-pentanol or 2-ethyl-1-butanol.

Among the inorganic nitrites which may be used, for example, are sodium nitrite or potassium nitrite, in aqueous acetic acid medium, at a temperature preferably from 0 to 5° C.

Among the organic nitrites which may be used, for example, is isoamyl nitrite, the reaction being carried out at room temperature, in a lower alcohol in the presence of an acid such as hydrochloric acid or acetic acid.

The catalytic hydrogenation of the compounds (4) is preferably carried out in a lower alcohol, in the presence of a catalyst such as palladium-on-charcoal, at a temperature generally of from 20 to 100° C.

When $R'_6$ is other than a methyl radical, and when $R'_1$ is other than a hydrogen atom (compounds of formula (I'B) below), process B corresponding to the following synthetic scheme:

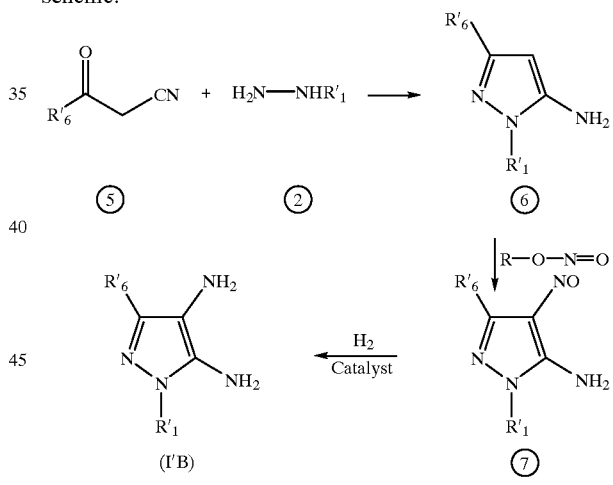

is preferably used, this synthetic scheme comprising reacting, in a first step, a β-keto acetonitrile (5) with a monosubstituted hydrazine (2), at a temperature generally of from 20 to 150° C., in an alcoholic solvent, in order to obtain the 5-aminopyrazole (6), which is then nitrosated in the 4-position, in a second step, to give a 4-nitro-5-aminopyrazole (7), which is itself then hydrogenated, in a third step, to lead to the 4,5-diaminopyrazoles of formula (I'B).

The solvents used according to this process B are the same as those mentioned for the process A described above.

The nitrosation and hydrogenation reactions are performed according to the conditions described for process A described above.

When $R'_6$ represents a radical which is of high steric bulk (compounds of formula (I'C) below), process C corresponding to the following synthetic scheme:

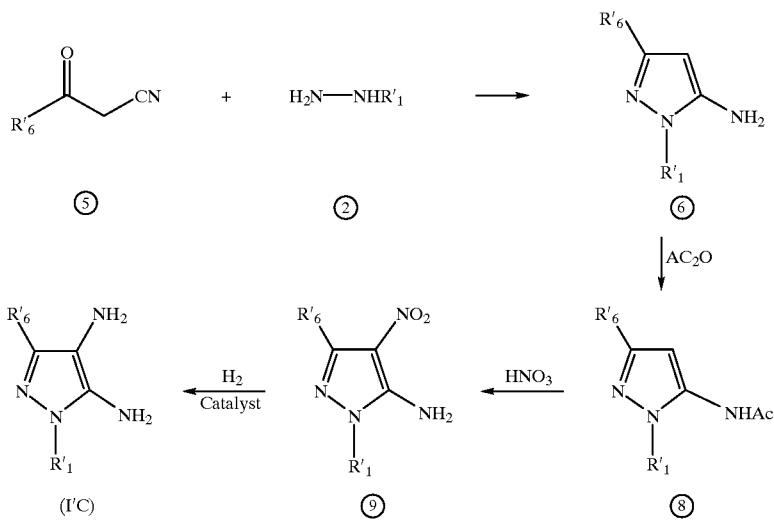

is preferably used, this synthetic scheme comprising reacting, in a first step, a β-keto acetonitrile (5) with a monosubstituted hydrazine (2) in order to obtain a 5-amino-pyrazole (6) according to the operating conditions mentioned for process B described above. The 5-amino-pyrazole (6) is then acetylated in the 5-position, in a second step, to lead to a 5-acetylaminopyrazole (8), which is itself then nitrated in the 4-position and deacetylated in the 5-position, in a third step, to give a 5-amino-4-nitropyrazole (9), preferably by fuming nitric acid in concentrated sulphuric medium, at a temperature preferably of from 0 to 5° C. The 5-amino-4-nitropyrazole (9) is then hydrogenated, in a fourth step, according to the operating conditions mentioned in process A above, to lead to the 4,5-diaminopyrazoles of formula (I'C).

When one of the radicals R'$_2$ or R'$_3$ is other than a hydrogen atom (compounds of formula (I'D) below), process D corresponding to the following synthetic scheme:

is preferably used, this synthetic scheme comprising reacting, in a first step, a β-keto ester (10) with a hydrazine (2) in order to obtain a 5-hydroxypyrazole (11), which is in equilibrium with its 5-pyrazolone tautomeric form, as described, for example, in Org. Synth., Edward C. Taylor (1976), 55, 73–7. The 5-hydroxypyrazole (11) is then nitrated in the 4-position, in a second step, and then chlorinated in the 5-position, in a third step, according to the method as described, for example, in U.S. Pat. No. 4,025, 530. The 5-chloro-4-nitropyrazole (13) then leads, in a fourth step, in the presence of a primary amine H$_2$N-R'$_3$, to a 5-amino-4-nitropyrazole (14) and then, in a fifth step, by catalytic hydrogenation according to the method described above for process A, to the 4,5-diaminopyrazoles of formula (I'D).

The examples which follow are intended to illustrate the invention without, however, limiting the scope thereof.

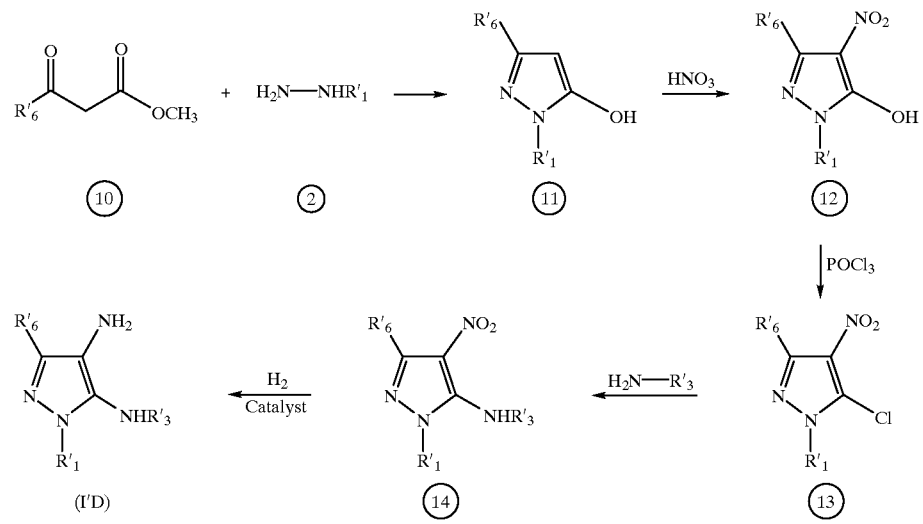

PREPARATION EXAMPLES

Preparation Example 1

Synthesis of 4,5-diamino-1,3-dimethylpyrazole dihydrochloride

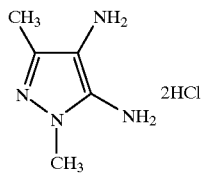

a) Preparation of 5-amino-1,3-dimethylpyrazole

To a solution of 16.5 g (0.2 mol) of 3-aminocrotononitrile in 40 cm³ of n-pentanol were added 12.9 g (0.28 mol) of methylhydrazine. The solution was maintained at reflux for 3 hours. The pentanol and the excess methylhydrazine were subsequently distilled off under reduced pressure. The beige precipitate obtained was taken up in 150 cm³ of heptane, filtered on a sinter funnel and then dried under vacuum at a temperature of 40° C. 13.5 g of 5-amino-1,3-dimethylpyrazole were obtained in the form of a beige solid, the melting point of which was from 80 to 81° C.

b) Preparation of 5-amino-1,3-dimethyl-4-nitrosopyrazole

To a solution of 11.1 g (0.1 mol) of 5-amino-1,3-dimethylpyrazole, obtained in the above step, in 125 cm³ of absolute ethanol were added dropwise 1cm³ of 12 N hydrochloric acid and then 13.5 cm³ of isoamyl nitrite, at 0° C. The solution was subsequently warmed to and left at room temperature for 4 hours. The reaction medium was then filtered on a sinter funnel and the precipitate obtained was washed with 100 cm³ of isopropyl ether. After drying under vacuum at room temperature, 7.5 g of 5-amino-1,3-dimethyl-4-nitroso-pyrazole were obtained in the form of an orange-coloured solid, the melting point of which was from 169 to 171° C.

c) Preparation of 4,5-diamino-1,3-dimethylpyrazole dihydrochloride

To a solution of 7 g (0.05 mol) of 5-amino-1,3-dimethylpyrazole, obtained in the above step, in 200 cm³ of ethanol were added 1.2 g of 5% by weight palladium-on-charcoal containing 50% water. The suspension was placed in a hydrogenator under a hydrogen pressure of 10 bar, at a temperature of 75° C. for 3 hours, with vigorous stirring. The reaction medium was poured into a solution of 50 cm³ of ethanol and 17 cm³ of 12 N hydrochloric acid cooled to 0° C. This solution was subsequently clarified by filtration on a sinter funnel and then evaporated to dryness under reduced pressure. The brown solid obtained was taken up, at reflux, in 45 cm³ of 5 N hydrochloric ethanol and 13 cm³ of water, and then cooled to room temperature. The white precipitate obtained was filtered on a sinter funnel and then dried under vacuum at room temperature. 5.7 g of 4,5-diamino-1,3-dimethylpyrazole dihydrochloride were obtained in the form of white crystals, the decomposition temperature of which was from 210 to 212° C. The elemental analysis calculated for $C_5H_{10}N_4.2HCl$ was:

|  | % | | | |
|---|---|---|---|---|
|  | C | H | N | Cl |
| Calculated | 30.17 | 6.08 | 28.14 | 35.62 |
| Found | 30.15 | 6.08 | 28.07 | 35.77 |

Preparation Example 2

Synthesis of 4,5-diamino-3-methyl-1-phenylpyrazole dihydrochloride

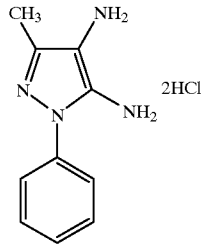

a) Preparation of 5-amino-3-methyl-4-nitroso-1-phenylpyrazole

To a solution of 17.3 g (0.1 mol) of 5-amino-3-methyl-1-phenylpyrazole in 200 cm³ of absolute ethanol were added dropwise 0.5 cm³ of 12 N hydrochloric acid and then 13.5 cm³ of isoamyl nitrite, at 0° C. The solution was then warmed to and left at room temperature for 4 hours. An orange-coloured solid crystallized out. This solid was filtered off on a sinter funnel and washed with 100 cm³ of isopropyl ether. After drying under vacuum at room temperature, 17 g of 5-amino-3-methyl-4-nitroso-1-phenylpyrazole were obtained in the form of an orange-coloured solid, the melting point of which was from 202 to 204° C.

b) Preparation of 4,5-diamino-3-methyl-1-phenylpyrazole dihydrochloride

To a solution of 10 g (0.05 mol) of 5-amino-3-methyl-4-nitroso-1-phenylpyrazole, obtained in the above step, in 80 cm³ of absolute ethanol and 20 cm³ of 2 N hydrochloric acid were added 1.2 g of 5% by weight palladium-on-charcoal containing 50% water. The suspension was placed in a hydrogenator under a hydrogen pressure of 10 bar, at a temperature of 75° C. for 3 hours, with vigorous stirring. The contents of the hydrogenator were subsequently recovered and filtered on a sinter funnel. The filtrate was poured into a solution, at 0° C., of 70 cm³ of absolute ethanol and 30 cm³ of 12 N hydrochloric acid and then evaporated to dryness. The residue was taken up in 100 cm³ of isopropyl ether: a beige solid crystallized out. This solid was filtered on a sinter funnel and then washed with 100 cm³ of isopropyl ether and purified by recrystallization from a mixture of 100 cm³ of water and 50 cm³ of 3.5 M ethanolic hydrochloric acid solution. The crystallized solid was filtered off on a sinter funnel, washed with 100 cm³ of isopropyl ether and dried under vacuum at room temperature. 8 g of 4,5-diamino-3-methyl-1-phenylpyrazole dihydrochloride were obtained in the form of a white solid, the melting point of which was from 208 to 210° C. The elemental analysis calculated for $C_{10}H_{17}N_4 \cdot 2HCl$ was:

|  | % | | | |
|---|---|---|---|---|
|  | C | H | N | Cl |
| Calculated | 45.99 | 5.40 | 21.45 | 27.15 |
| Found | 46.17 | 5.40 | 21.32 | 27.10 |

Preparation Example 3

Synthesis of 4,5-diamino-1-methyl-3-phenylpyrazole dihydrochloride

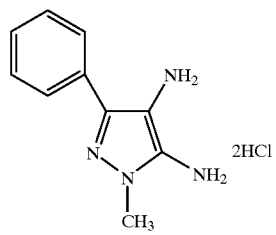

a) Preparation of 5-amino-1-methyl-3-phenylpyrazole

To a solution of 29 g (0.2 mol) of benzoylacetonitrile in 100 cm³ of n-pentanol were added 14.7 cm³ (0.28 mol) of methylhydrazine and the mixture was heated at reflux for 2 hours. The n-pentanol and the excess methylhydrazine were subsequently distilled off under reduced pressure. A beige solid was obtained, which was taken up in 100 cm³ of heptane at room temperature and filtered off on a sinter funnel. After drying under vacuum at a temperature of 40° C., 27 g of 5-amino-1-methyl-3-phenylpyrazole were obtained in the form of a beige solid, the melting point of which was from 104 to 106° C.

b) Preparation of 5-amino-1-methyl-4-nitroso-3-phenylpyrazole

To a solution of 17.3 g (0.1 mol) of 5-amino-1-methyl-3-phenylpyrazole, obtained in the above step, in 200 cm³ of absolute ethanol were added dropwise 0.5 cm³ of 12 N hydrochloric acid and then 13.5 cm³ of isoamyl nitrite, at 0° C. The solution was subsequently warmed to and left at room temperature for 4 hours. An orange-coloured solid crystallized out. This was filtered off on a sinter funnel and washed with 100 cm³ of isopropyl ether. After drying under vacuum at room temperature, 17 g of 5-amino-1-methyl-4-nitroso-3-phenylpyrazole were obtained in the form of an orange-coloured solid, the melting point of which was from 224 to 226° C.

c) Preparation of 4,5-diamino-1-methyl-3-phenylpyrazole dihydrochloride

To a solution of 10 g (0.05 mol) of 5-amino-1-methyl-4-nitroso-3-phenylpyrazole, obtained in the above step, in 80 cm³ of absolute ethanol and 20 cm³ of 2 N hydrochloric acid solution were added 1.2 g of 5% by weight palladium-on-charcoal containing 50% water. The suspension was placed in a hydrogenator under a hydrogen pressure of 10 bar, at a temperature of 75° C. for 3 hours, with vigorous stirring. The contents of the hydrogenator were recovered and filtered on a sinter funnel. The filtrate was poured into a solution of 70 cm³ of absolute ethanol and 30 cm³ of 12 N hydrochloric acid cooled to 0° C. A white solid precipitated out. This precipitate was filtered off on a sinter funnel and then washed with 100 cm³ of isopropyl ether. After drying under vacuum at room temperature, 10 g of 4,5-diamino-1-methyl-3-phenylpyrazole dihydrochloride were obtained, which product was then purified by recrystallization from a mixture of 30 cm³ of water and 50 cm³ of 3.5 M ethanolic hydrochloric acid solution. The recrystallized solid was filtered off on a sinter funnel, washed with 100 cm³ of isopropyl ether and dried under vacuum at room temperature. 8 g of 4,5- diamino-1-methyl-3-phenylpyrazole dihydrochloride were obtained in the form of a white solid, the melting point of which was from 218 to 220° C. The elemental analysis calculated for $C_{10}H_{12}N_4 \cdot 2HCl$ was:

|  | % | | | |
|---|---|---|---|---|
|  | C | H | N | Cl |
| Calculated | 45.99 | 5.40 | 21.45 | 27.15 |
| Found | 46.27 | 5.60 | 21.32 | 27.10 |

Preparation Example 4

Synthesis of 4-amino-1,3-dimethyl-5-hydrazinopyrazole dihydrochloride

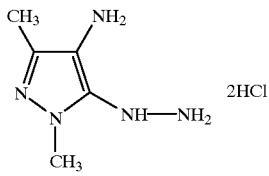

A suspension of 8.6 g (0.05 mol) of 1,3-dimethyl-5-hydrazino-4-nitropyrazole and 1.5 g of 5% by weight palladium-on-charcoal containing 50% water in 200 cm³ of ethanol was placed in a hydrogenator. After stirring under a hydrogen pressure of 10 bar, at a temperature of 75° C. for 3 hours, the reaction medium was poured into a solution of 60 cm³ of ethanol and 20 cm³ of 12 N hydrochloric acid cooled to 0° C. The solution was clarified by filtration on a sinter funnel and then evaporated to dryness under reduced pressure. The brown solid obtained was taken up, at reflux, in 50 cm³ of 5 N hydrochloric ethanol and 14 cm³ of water and was then cooled to room temperature. The white precipitate obtained was filtered off on a sinter funnel and then dried under vacuum at room temperature. 9.5 g of 4-amino-1,3-dimethyl-5-hydrazinopyrazole dihydrochloride were obtained in the form of white crystals, the melting point of which was from 202 to 204° C. The elemental analysis calculated for $C_5H_{11}N_5 \cdot 2HCl$ was:

|  | % | | | |
|---|---|---|---|---|
|  | C | H | N | Cl |
| Calculated | 28.05 | 6.12 | 32.71 | 33.12 |
| Found | 28.52 | 6.20 | 32.96 | 32.88 |

Preparation Example 5

Synthesis of 1-benzyl-4,5-diamino-3-methylpyrazole dihydrochloride

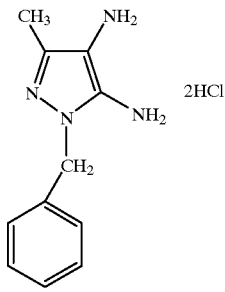

a) Preparation of 5-amino-1-benzyl-3-methylpyrazole

To a solution of 16.4 g (0.2 mol) of 3-aminocrotononitrile in 100 cm³ of n-pentanol were added 26.9 g (0.22 mol) of benzylhydrazine and the mixture was then heated at reflux for 12 hours. The n-pentanol was subsequently distilled off under reduced pressure and a thick oil was obtained, which was purified by chromatography on silica gel. A pale yellow solid was obtained, which was crystallized from isopropyl ether and was then filtered on a sinter funnel. After drying under vacuum at 40° C., 17 g of the expected product were obtained in the form of a pale yellow solid, the melting point of which was from 76 to 78° C.

b) Preparation of 5-amino-1-benzyl-3-methyl-4-nitrosopyrazole

To a solution of 18.7 g (0.1 mol) of 5-amino-1-benzyl-3-methylpyrazole, obtained in the above step, in 200 cm³ of an absolute ethanol were added dropwise 0.5 cm³ of 12 N hydrochloric acid and then 13.5 cm³ of isoamyl nitrite, at 0° C. The solution was subsequently warmed to and left at room temperature for 4 hours. An orange-coloured solid crystallized out. It was filtered off on a sinter funnel and washed with 100 cm³ of ethanol and then with 100 cm³ of isopropyl ether. After drying under vacuum at room temperature, 13 g of the expected product were obtained in the form of an orange-coloured solid, the melting point of which was from 178 to 180° C.

c) Preparation of 1-benzyl-4,5-diamino-3-methylpyrazole dihydrochloride

To a solution of 5 g (0.02 mol) of 5-amino-1-benzyl-3-methyl-5-nitrosopyrazole, obtained in the above step, in 200 cm³ of methanol was added 0.9 g of 5% by weight palladium-on-charcoal containing 50% water. The suspension was placed in a hydrogenator under a pressure of 20 bar of hydrogen, at room temperature for 3 hours, with vigorous stirring. The contents of the hydrogenator were removed and filtered on a sinter funnel. The filtrate was subsequently poured into 100 cm³ of 3.5 M hydrochloric ethanol solution. This solution was concentrated under vacuum. A thick oil was obtained, which was crystallized by addition of 50 cm³ of acetone. A solid was obtained, which was filtered off on a sinter funnel. After drying under vacuum at room temperature, 6 g of 1-benzyl-4,5-diamino-3-methylpyrazole dihydrochloride were obtained in the form of a white solid, the melting point of which was from 190 to 192° C. The elemental analysis calculated for $C_{11}H_{14}N_4 \cdot 2HCl$ was:

|  | % | | | |
|---|---|---|---|---|
|  | C | H | N | Cl |
| Calculated | 48.01 | 5.86 | 20.36 | 25.77 |
| Found | 48.03 | 5.90 | 20.40 | 25.75 |

Preparation Example 6

Synthesis of 4,5-diamino-1-methyl-3-tert-butylpyrazole dihydrochloride

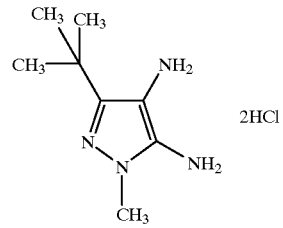

a) Preparation of 5-amino-1-methyl-3-tert-butylpyrazole

To a solution of 12.5 g (0.1 mol) of 4,4-dimethyl-3-oxopentanenitrile in 50 cm³ of n-propanol were added, at room temperature, 4.6 g (0.1 mol) of methylhydrazine. The reaction medium was maintained at reflux for 1 hour and then cooled to room temperature. The white solid obtained was filtered off on a sinter funnel and then washed with isopropyl ether. After drying under vacuum at 40° C., 10 g of the expected product were obtained in the form of a beige solid, the melting point of which was 157° C.

b) Preparation of 5-acetamido-1-methyl-3-tert-butylpyrazole

To a solution of 10 g (0.065 mol) of 5-amino-1-methyl-3-tert-butylpyrazole, obtained in the above step, in 25 cm³ of acetic acid were added, at room temperature, 13.5 cm³ (0.13 mol) of acetic anhydride. After stirring for 1 hour, the reaction mixture was poured onto 100 cm³ of ice. The solution was extracted three times with 100 cm³ of dichloromethane and the organic phase was dried over sodium sulphate and then distilled under vacuum on a rotary evaporator. The solid obtained was taken up in 100 cm³ of isopropyl ether, filtered on a sinter funnel and then dried under vacuum at 40° C. 12 g of the expected product were obtained in the form of a beige solid, which product was recrystallized from 30 cm³ of ethyl acetate in order to isolate 8.5 g of the expected product in the form of white crystals, the melting point of which was 138° C.

c) Preparation of 5-amino-1-methyl-4-nitro-3-tert-butylpyrazole

To 30 cm³ of concentrated sulphuric acid were added 8.5 g (0.044 mol) of 5-acetamido-1-methyl-3-tert-butylpyrazole, at 5° C. with vigorous stirring, followed by 2.5 cm³ (0.066 mol) of fuming nitric acid. After stirring for 2 hours, the reaction mixture was poured onto 100 g of ice and stirred for 30 minutes. The solid obtained was filtered off on a sinter funnel, washed with 20 cm³ of water and then dried under vacuum at 40° C. 8.5 g of the expected product were obtained in the form of a yellow solid, the melting point of which was 124° C.

d) Preparation of 4,5-diamino-1-methyl-3-tert-butylpyrazole dihydrochloride

A suspension of 8.5 g (0.035 mol) of 5-amino-1-methyl-4-nitro-3-tert-butylpyrazole and 1.5 g of 5% by weight palladium-on-charcoal containing 50% water in 200 cm³ of ethanol was placed in a hydrogenator. After stirring for 3 hours under a hydrogen pressure of 10 bar, at a temperature of 75° C., the reaction medium was poured into a solution, precooled to 0° C., of 60 cm³ of ethanol and 20 cm³ of 12 N hydrochloric acid. The solution was clarified by filtration on a sinter funnel and then evaporated to dryness under reduced pressure. The brown solid obtained was taken up, at reflux, in 35 cm³ of 5 N hydrochloric ethanol and 11 cm³ of water and then cooled to room temperature. The white crystals obtained were filtered off on a sinter funnel and then dried under vacuum at room temperature. 4.9 g of the expected product were obtained in the form of white crystals, the melting point of which was 260° C. The elemental analysis for $C_8H_{10}N_4 \cdot 2HCl$ was:

|  | % | | | |
|---|---|---|---|---|
|  | C | H | N | Cl |
| Calculated | 39.84 | 7.52 | 23.23 | 29.40 |
| Found | 39.73 | 7.63 | 23.16 | 29.20 |

Preparation Example 7

Synthesis of 4,5-diamino-3-methyl-1-tert-butylpyrazole dihydrochloride

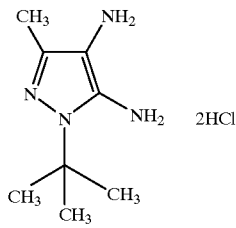

a) Preparation of 5-amino-3-methyl-1-tert-butylpyrazole

To a solution of 16.4 g (0.2 mol) of 3-aminocrotononitrile in 100 cm³ of n-pentanol were added 19.4 g (0.22 mol) of tert-butylhydrazine. This solution was heated at reflux for 20 hours. The n-pentanol was subsequently distilled off under reduced pressure. A pale yellow solid was obtained, which was taken up in 100 cm³ of isopropyl ether at room temperature and filtered on a sinter funnel. After drying under vacuum at 40° C., 18 g of the expected product were obtained in the form of a pale yellow solid, the melting point of which was from 172 to 175° C.

b) Preparation of 5-amino-3-methyl-4-nitroso-1-tert-butylpyrazole

To a solution of 15.3 g (0.1 mol) of 5-amino-3-methyl-1-tert-butylpyrazole, obtained in the above step, in 200 cm³ of absolute ethanol were added dropwise 0.5 cm³ of 12 N hydrochloric acid and then 13.5 cm³ (0.1 mol) of isoamyl nitrite, at 0° C. The solution was subsequently warmed to and left at room temperature for 4 hours.

The ethanol was evaporated off under a pressure of 175 mbar, at 40° C. An orange-coloured solid was crystallized from heptane at 0° C. and then filtered off on a sinter funnel. After drying under vacuum at room temperature, 11 g of the expected product were obtained in the form of an orange-coloured solid, the melting point of which was 120° C.

c) Preparation of 4,5-diamino-3-methyl-1-tert-butylpyrazole dihydrochloride

To a solution of 9 g (0.05 mol) of 5-amino-3-methyl-4-nitroso-1-tert-butylpyrazole, obtained in the above step, in 600 cm³ of absolute ethanol were added 2 g of 5% by weight palladium-on-charcoal containing 50% water. The suspension was placed in a hydrogenator under a pressure of 20 bar of hydrogen, at room temperature for 4 hours, with vigorous stirring. The contents of the hydrogenator were removed and filtered on a sinter funnel. The filtrate was subsequently poured into 100 cm³ of 3.5 M hydrochloric ethanol solution. This solution was concentrated under vacuum to the point at which crystallization commenced. The crystals were subsequently washed with 3.5 M hydrochloric ethanol solution and then filtered off on a sinter funnel. A white solid was obtained, which was recrystallized from a mixture of 40 cm³ of 3.5 M hydrochloric ethanol and 12 cm³ of distilled water. After drying under vacuum at room temperature, 8 g of the expected product were obtained in the form of white crystals, the melting point of which was from 252 to 255° C. The elemental analysis for $C_8H_{16}N_4 \cdot 2HCl$ was:

|  | % | | | |
|---|---|---|---|---|
|  | C | H | N | Cl |
| Calculated | 39.84 | 7.52 | 23.23 | 29.40 |
| Found | 39.70 | 7.49 | 23.37 | 29.44 |

Preparation Example 8

Synthesis of 4,5-diamino-1-β-hydroxyethyl-3-methylpyrazole dihydrochloride

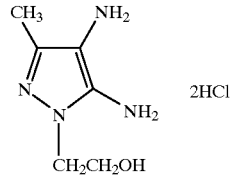

a) Preparation of 5-amino-1-(β-hydroxyethyl)-3-methylpyrazole

To a solution of 16.4 g (0.2 mol) of 3-aminocrotononitrile in 100 cm³ of n-pentanol were added 16.7 g (0.22 mol) of β-hydroxyethylhydrazine and the mixture was then heated at reflux for 12 hours. The n-pentanol was subsequently distilled off under reduced pressure. A thick oil was obtained, which crystallizes by addition of 150 cm³ of isopropyl ether. A beige solid was obtained, which was filtered off on a sinter funnel. After drying under vacuum at 40° C., 18 g of the expected product were obtained in the form of a beige solid, the melting point of which was from 66 to 68° C.

b) Preparation of 5-amino-1-(β-hydroxyethyl)-3-methyl-4-nitrosopyrazole

To a solution of 14.1 g (0.1 mol) of 5-amino-1-(β-hydroxyethyl)-3-methylpyrazole, obtained in the above step, in 200 cm³ of absolute ethanol were added dropwise 0.5 cm³ of 12 N hydrochloric acid and then 13.5 cm³ of isoamyl nitrite, at 0° C. The solution was subsequently warmed to and left at room temperature for 4 hours. A red solid crystallized out and was filtered off on a sinter funnel and then washed with 100 cm³ of ethanol, and then with 100 cm³ of isopropyl ether. After drying under vacuum at room temperature, 10.5 g of the expected product were obtained in the form of red crystals, the melting point of which was from 170 to 175° C.

c) Preparation of 4,5-diamino-1-(β-hydroxyethyl)-3-methylpyrazole dihydrochloride To a solution of 8.5 g (0.05 mol) of the product obtained in the above step, in 800 cm³ of methanol, were added 2 g of 5% by weight palladium-on-charcoal containing 50% water. The suspension was placed in a hydrogenator under a pressure of 20 bar of hydrogen, at 30° C. for 4 hours, with vigorous stirring. The contents of the hydrogenator were subsequently removed and filtered on a sinter funnel in 100 cm³ of 6 M hydrochloric ethanol solution. This solution was concentrated under vacuum. A thick oil was obtained, which crystallized by addition of 50 cm³ of isopropyl ether. A white solid was obtained, which was recrystallized from a mixture of 45 cm³ of 6 M hydrochloric ethanol and 3.5 cm³ of distilled water. After drying under vacuum at room temperature, 7.5 g of the expected product were obtained in the form of white crystals, the melting point of which was from 190 to 193° C. The elemental analysis calculated for $C_8H_{12}N_4O.2HCl$ was:

|  | % | | | | |
| --- | --- | --- | --- | --- | --- |
|  | C | H | N | O | Cl |
| Calculated | 31.46 | 6.16 | 24.45 | 6.98 | 30.95 |
| Found | 31.44 | 6.21 | 24.10 | 7.07 | 30.98 |

Preparation Example 9

Synthesis of 4-amino-5-(2'-aminoethyl)amino-1,3-dimethylpyrazole dihydrochloride a) Preparation of 5-[(2'-aminoethyl)amino]-1,3-dimethyl-4-nitropyrazole hydrochloride To a solution of 17.5 g (0.1 mol) of 5-chloro-1,3-dimethylpyrazole in 200 cm³ of n-propanol were added 7.3 cm³ (0.11 mol) of ethylenediamine. This solution was heated at reflux for 4 hours. The solution was subsequently cooled to and left at room temperature for 15 hours. A bright yellow solid crystallized out and was then filtered off on a sinter funnel. After drying under vacuum at 40° C., 19 g of the expected product were obtained in the form of a yellow solid, the melting point of which was 235° C.

b) Preparation of 4-amino-5-(2'-aminoethyl)amino-1,3-dimethylpyrazole dihyrochloride To a solution of 10 g (0.04 mol) of 5-[(2'-aminoethyl)amino]-1,3-dimethyl-4-nitropyrazole hydrochloride, obtained in the above step, in 20 cm³ of methanol were added 2 g of 5% by weight palladium-on-charcoal containing 50% water. The suspension was placed in a hydrogenator under a pressure of 10 bar of hydrogen, at 40° C. for 3 hours, with vigorous stirring. The contents of the hydrogenator were removed and filtered on a sinter funnel in 100 cm³ of 3.5 M hydrochloric ethanol solution. This solution was concentrated under vacuum. A thick oil was obtained, which crystallized by addition of 50 cm³ of isopropyl ether. The solid formed was filtered off on a sinter funnel and then washed with 20 cm³ of isopropyl ether and purified by recrystallization from a mixture of 33 cm³ of absolute ethanol and 16 cm³ of 6 M hydrochloric acid. The crystallized solid was filtered off on a sinter funnel, washed with 50 cm³ of isopropyl ether and dried under vacuum at room temperature. 5 g of 4-amino-5-(2'-aminoethyl)amino-1,3-dimethylpyrazole dihydrochloride were obtained in the form of a white solid, the melting point of which was from 238 to 240° C.

The elemental analysis for $C_7H_{15}N_5.2HCl$ was:

|  | % | | | |
| --- | --- | --- | --- | --- |
|  | C | H | N | Cl |
| Calculated | 34.72 | 7.08 | 28.92 | 29.28 |
| Found | 34.70 | 7.05 | 28.89 | 29.50 |

APPLICATION EXAMPLES

Examples 10 to 18 of Dyeing in Alkaline Medium

The following dye compositions, in accordance with the invention, were prepared (contents in grams):

| COMPOSITION | 10 | 11 | 12 | 13 | 14 | 15 | 16 | 17 | 18 |
| --- | --- | --- | --- | --- | --- | --- | --- | --- | --- |
| 4,5-diamino-1,3-dimethylpyrazole dihydrochloride | 0.597 | 0.597 | 0.597 | 0.597 | | | | | |
| 4-amino-1,3-dimethyl-5-hydrazinopyrazole dihydrochloride | | | | | 0.642 | 0.642 | | | |
| 4,5-diamino-3-methyl-1-phenylpyrazole dihydrochloride | | | | | | | 0.783 | | |
| 4,5-diamino-3-methyl-1-tert-butylpyrazole dihydrochloride | | | | | | | | 0.742 | |
| 4,5-diamino-1-methyl-3-tert-butylpyrazole dihydrochloride | | | | | | | | | 0.724 |
| 3-aminophenol | 0.327 | | | | 0.501 | | | | |
| 5-N-(β-hydroxyethyl)amino-2-methylphenol | | | | | | | | | |
| 2,4-diamino-1-β-hydroxyethyloxybenzene dihydrochloride | | | | | | 0.723 | | | |
| 2,6-dihydroxy-4-methylpyridine dihydrochloride monohydrate | | 0.539 | | | | | | | |
| 2-methyl-5-aminophenol | | | | | | | | 0.369 | |
| 6-hydroxyindoline hydrochloride | | | 0.515 | | | | | | |
| 4-hydroxyindole | | | | | | | 0.399 | | |
| 4-hydroxy-N-methylindole | | | | 0.442 | | | | | |
| Common dye support | (*) | (*) | (*) | (*) | (*) | (*) | (*) | (*) | (*) |
| Demineralized water qs | 100 g | 100 g | 100 g | 100 g | 100 g | 100 g | 100 g | 100 g | 100 g |

BASES COUPLERS ( ) common dye support:

| | |
|---|---|
| Oleyl alcohol polyglycerolated with 2 mol of glycerol | 40 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen O12 by the company Akzo | 7.0 g |
| Diethylaminopropyl laurylaminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Aqueous sodium metabisulphite solution containing 35% A.M. | 0.455 g A.M. |
| Ammonium acetate | 0.8 g |
| Antioxidant, sequestering agent qs | |
| Fragrance, preserving agent qs | |
| Aqueous ammonia containing 20% NH3 | 10 g |

Each dye composition 10 to 18 was mixed, at the time of use, with an equal amount by weight of an oxidizing composition consisting of 20-volumes aqueous-peroxide solution (6% by weight).

Each resulting composition was applied for 30 minutes to locks of natural grey hair containing 90% white hairs. The locks of hair were subsequently rinsed, washed with a saturated shampoo and then dried.

The locks of hair were dyed in the shades featured in the table below:

| EXAMPLE | pH OF THE MIXTURE | SHADE ON NATURAL HAIR |
|---|---|---|
| 10 | 9.8 | Iridescent |
| 11 | 9.9 | Coppery golden |
| 12 | 9.9 | Slightly iridescent blonde |
| 13 | 9.9 | Violet |
| 14 | 10.0 | Iridescent |
| 15 | 9.8 | Purplish blue |
| 16 | 9.8 | Dark purple |
| 17 | 9.7 | Iridescent |
| 18 | 9.9 | Blue |

Examples 19 and 20 of Dyeing in Acidic Medium

The following dye compositions, in accordance with the invention, were prepared (contents in grams):

| COMPOSITION | 19 | 20 |
|---|---|---|
| BASES | | |
| 4,5-diamino-1,3-dimethylpyrazole dihydrochloride | 0.597 | |
| 4-amino-1,3-dimethyl-5-hydrazinopyrazole dihydrochloride | | 0.642 |
| COUPL | | |
| 2,4-diamino-1-β-hydroxyethylozybenzene dichlorohydride | 0.723 | |
| 2-methyl-5-aminophenol | | 0.369 |

| COMPOSITION | 19 | 20 |
|---|---|---|
| Common dye support | () | () |
| Demineralized water qs | 100 g | 100 g |

( ) common dye support:

| | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen O12 by the company Akzo | 7.0 g |
| Diethylaminopropyl laurylaminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Aqueous sodium metabisulphite solution containing 35% A.M. | 0.455 g A.M. |
| Ammonium acetate | 0.8 g |
| Antioxidant, sequestering agent qs | |
| Fragrance, preserving agent qs | |
| Mondethanolamine qs pH 9.8 | |

Each dye composition was mixed, at the time of use, with an equal amount by weight of an oxidizing composition consisting of 20-volumes aqueous-peroxide solution (6% by weight), and the pH of which had been adjusted to between 1 and 1.5 with 2.5 g of orthophosphoric acid per 100 g of aqueous hydrogen peroxide.

Each resulting composition was applied for 30 minutes to locks of natural grey hair containing 90% white hairs. The locks of hair were subsequently rinsed, washed with a standard shampoo and then dried.

The locks of hair were dyed in the shades featured in the table below:

| EXAMPLE | pH OF THE MIXTURE | SHADE ON NATURAL HAIR |
|---|---|---|
| 19 | 6.9 | Purplish blue |
| 20 | 6.5 | Iridescent |

Example 21 of Dyeing in Air

The following dye composition, in accordance with the invention, was prepared:

| | |
|---|---|
| 4,5-Diamino-1,3-dimethylpyrazole dihydrochloride | 0.398 g |
| 2,4-Diamino-1-β-hydroxyethyloxy benzene dihydrochloride | 0.482 g |
| Ethyl alcohol | 10 g |
| Monoethanolamine | 2 g |
| Demineralized water qs | 100 g |

This composition was applied for 30 minutes to locks of natural grey hair containing 90% white hairs. After rinsing and drying, the locks were dyed in a purplish ash shade.

What is claimed is:

1. A 3-substituted 4,5-diaminopyrazole or an acid-addition salt thereof, wherein said 3-substituted 4,5,-diaminopyrazole is:

4,5-diamino-3-hydroxymethyl-1-phenylpyrazole,
4,5-diamino-3-hydroxymethyl-1-(2'-methoxyphenyl)-pyrazole,
4,5-diamino-3-hydroxymethyl-1-(3'-methoxyphenyl)-pyrazole,
4,5-diamino-3-hydroxymethyl-1-(4'-methoxyphenyl)-pyrazole,
4,5-diamino-3-methyl-1-(2'-methoxyphenyl)pyrazole,
4,5-diamino-3-methyl-1-(3'-methoxyphenyl)pyrazole,
4,5-diamino-3-methyl-1-(4'-methoxyphenyl)pyrazole,
3-aminomethyl-4,5-diamino-1-methylpyrazole,
3-aminomethyl-4,5-diamino-1-ethylpyrazole,
3-aminomethyl-4,5-diamino-1-isopropylpyrazole,
3-aminomethyl-4,5-diamino-1-tert-butylpyrazole,
4,5-diamino-3-dimethylaminomethyl-1-methylpyrazole,
4,5-diamino-3-dimethylaminomethyl-1-ethylpyrazole,
4,5-diamino-3-dimethylaminomethyl-1-isopropyl-pyrazole,
4,5-diamino-3-dimethylaminomethyl-1-tert-butyl-pyrazole,
4,5-diamino-3-ethylaminomethyl-1-methylpyrazole,
4,5-diamino-3-ethylaminomethyl-1-ethylpyrazole,
4,5-diamino-3-ethylaminomethyl-1-isopropylpyrazole,
4,5-diamino-3-ethylaminomethyl-1-tert-butylpyrazole,
4,5-diamino-3-methylaminomethyl-1-methylpyrazole,
4,5-diamino-3-methylaminomethyl-1-isopropylpyrazole,
4,5-diamino-1-ethyl-3-methylaminomethylpyrazole,
1-tert-butyl-4,5-diamino-3-methylaminomethyl-pyrazole,
4,5-diamino-3-((β-hydroxyethyl)aminomethyl)-1-methyl-pyrazole,
4,5-diamino-3-((β-hydroxyethyl)aminomethyl)-1-isopropylpyrazole,
4,5-diamino-1-ethyl-3-((β-hydroxyethyl)aminomethyl)-pyrazole,
1-tert-butyl-4,5-diamino-3-((β-hydroxyethyl)aminomethyl)-pyrazole,
4-amino-5-(β-hydroxyethyl)amino-1,3-dimethylpyrazole,
4-amino-5-(β-hydroxyethyl)amino-1-isopropyl-3-methyl-pyrazole,
4-amino-5-(β-hydroxyethyl)amino-1-ethyl-3-methyl-pyrazole,
4-amino-5-(β-hydroxyethyl)amino-1-tert-butyl-3-methylpyrazole,
4-amino-5-(β-hydroxyethyl)amino-1-phenyl-3-methyl-pyrazole,
4-amino-5-(β-hydroxyethyl)amino-1-(2'-methoxyphenyl)-3-methylpyrazole,
4-amino-5-(β-hydroxyethyl)amino-1-(3'-methoxyphenyl)-3-methylpyrazole,
4-amino-5-(β-hydroxyethyl)amino-1-(4'-methoxyphenyl)-3-methylpyrazole,
4-amino-5-(β-hydroxyethyl)amino-1-benzyl-3-methyl-pyrazole,
4-amino-1-ethyl-3-methyl-5-methylaminopyrazole,
4-amino-1-tert-butyl-3-methyl-5-methylaminopyrazole,
1-(4'-chlorobenzyl)-4,5-diamino-3-methylpyrazole,
4-amino-1-ethyl-3-methyl-5-methylaminopyrazole, or
4-amino-5-(2'-aminoethyl)amino-1,3-dimethylpyrazole.

2. A 3-substituted 4,5-diaminopyrazole according to claim 1, wherein said 3-substituted 4,5-diaminopyrazole is:

4-amino-5-(2'-aminoethyl)amino-1,3-dimethyl-pyrazole.

3. A multi compartment device or multi-compartment dyeing kit, a first compartment of which contains a dye composition and a second compartment of which contains an oxidizing composition, wherein said dye composition comprises, in a medium suitable for dyeing, at least one oxidation base selected from a 3-substituted 4,5-diaminopyrazole of the following formula (I) and an acid-addition salt thereof:

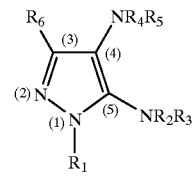

(I)

in which:

$R_1$, $R_2$, $R_3$, $R_4$ and $R_5$ which may be identical or different, represent a hydrogen atom; a linear or branched $C_1$–$C_6$ alkyl radical; a $C_2$–$C_4$ hydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; or a radical

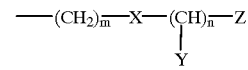

in which m and n are integers, which may be identical or different, from 1 to 3 inclusive, X represents an oxygen atom or an NH group, Y represents a hydrogen atom or a methyl radical and Z represents a methyl radical, a group OR or NRR' in which R and R', which may be identical or different, denote a hydrogen atom, a methyl radical or an ethyl radical, it being understood that when $R_2$ represents a hydrogen atom, $R_3$ may then also represent an amino or $C_1$–$C_4$ alkylamino radical, $R_6$ represents a linear or branched $C_1$–$C_6$ alkyl radical; a $C_1$–$C_4$ hydroxyalkyl radical; a $C_1$–$C_4$ aminoalkyl radical; a $C_1$–$C_4$ dialkylamino ($C_1$–$C_4$) alkyl radical; a $C_1$–$C_4$ alkylamino ($C_1$–$C_4$) alkyl radical; a $C_1$–$C_4$ hydroxyalkylamino ($C_1$–$C_4$) alkyl radical; a $C_1$–$C_4$ alkoxymethyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, nitro, trifluoromethyl, amino or $C_1$–$C_4$ alkylamino radical; a heterocycle which is thiophene, furan or pyridine, or alternatively a radical —$(CH_2)_p$—O—$(CH_2)_q$—OR", in which p and q are integers, which may be identical or different, from 1 to 3 inclusive and R" represents a hydrogen atom or a methyl radical, wherein said at least one oxidation base is present in an amount effective to dye said keratin fibers, it being understood that, in the above formula (I):

at least one of the radicals $R_2$, $R_3$, $R_4$ and $R_5$ represents a hydrogen atom, when $R_2$, or respectively $R_4$, represents a substituted or unsubstituted phenyl radical or a benzyl radical or a radical

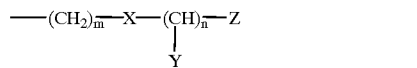   5

$R_3$, or respectively $R_5$, cannot then represent any of these three radicals, when $R_4$ and $R_5$ simultaneously represent a hydrogen atom, $R_1$ can then form, with $R_2$ and $R_3$, a hexahydropyrimidine or tetrahydroimidazole heterocycle optionally substituted with a $C_1$–$C_4$ alkyl or 1,2,4-tetrazole radical, when $R_1$ is hydrogen, a $C_1$–$C_6$ alkyl radical, or a $C_2$–$C_4$ hydroxyalkyl radical and when $R_6$ is a $C_1$–$C_6$ alkyl radical, a $C_1$–$C_4$ hydroxyalkyl radical, a phenyl radical, a substituted phenyl radical, a benzyl radical or a substituted benzyl radical, then at least one of $R_2$, $R_3$, $R_4$ or $R_5$ is not hydrogen, when $R_2$, $R_3$, $R_4$ and $R_5$ represent a hydrogen atom or a $C_1$–$C_6$ alkyl radical, $R_1$ or $R_6$ may then also represent a 2-, 3- or 4-pyridyl, 2- or 3-thienyl or 2- or 3-furyl heterocyclic residue optionally substituted with a methyl radical or alternatively a cyclohexyl radical.

\* \* \* \* \*